United States Patent [19]
Niino et al.

[11] Patent Number: 5,484,567
[45] Date of Patent: Jan. 16, 1996

[54] METHOD FOR PRODUCING A THIN-WALLED MOLDED ARTICLE OF A POLYACETAL RESIN

[75] Inventors: Masahiko Niino; Sadao Ibe, both of Kurashiki, Japan

[73] Assignee: Asahi Kasei Kogyo Kabushiki Kaisha, Japan

[21] Appl. No.: 244,952

[22] PCT Filed: Nov. 12, 1993

[86] PCT No.: PCT/JP93/01651

§ 371 Date: Jun. 13, 1994

§ 102(e) Date: Jun. 13, 1994

[87] PCT Pub. No.: WO94/09676

PCT Pub. Date: May 11, 1994

[30] Foreign Application Priority Data

Nov. 13, 1992 [JP] Japan ..................... 4-303565

[51] Int. Cl.⁶ .............. B29C 45/00; C08L 59/00
[52] U.S. Cl. .............. 264/328.1; 264/328.18; 264/331.11
[58] Field of Search .............. 264/328.1, 328.18, 264/331.11

[56] References Cited

U.S. PATENT DOCUMENTS

| | | |
|---|---|---|
| 3,976,605 | 8/1976 | Matsunaga et al. |
| 4,051,096 | 9/1977 | Koseki et al. |
| 5,131,827 | 7/1992 | Tasaka ................ 264/328.1 |

FOREIGN PATENT DOCUMENTS

| | | |
|---|---|---|
| 47-11136 | 6/1972 | Japan. |
| 57-11017 | 1/1982 | Japan. |
| 62-187751 | 8/1987 | Japan. |

*Primary Examiner*—Jill L. Heitbrink
*Attorney, Agent, or Firm*—Pennie & Edmonds

[57] ABSTRACT

The present invention provides a method for producing a thin-walled molded article of a polyacetal resin comprising adding 10 to 1000 ppm of boron nitride having an average particle diameter of 1 to 10 μm and a content of diboron trioxide of 0.005 to 1.0% by weight to a polyacetal resin and molding an article having a maximum wall thickness of 0.2 to 1 mm by injection molding.

The present invention can provide a molded article of a polyacetal resin having little warpage at a high temperature and humidity.

2 Claims, 4 Drawing Sheets

METHOD FOR PRODUCING A THIN-WALLED MOLDED ARTICLE OF A POLYACETAL RESIN

TECHNICAL FIELD

The present invention relates a method for producing a thin-walled molded article of a polyacetal resin having excellent dimensional stability to temperature and humidity changes.

BACKGROUND ART

A polyacetal resin is widely used as an engineering resin because of its excellent mechanical strength, fatigue resistance, electrical properties and the like.

However, since the polyacetal resin has high crystallizability, it has drawbacks that a molded article of it undergoes warpage or sink marks by heat dissipation immediately after injection molding and after heat dissipation (cooling), the molded article further undergoes dimensional changes such as warpage when it is exposed to a high temperature and humidity. Particularly, in case of a thin-walled molded article, remarkable warpage appears on it.

The present invention has been completed based on finding that warpage of a thin-walled molded article is reduced when the amorphous layer, which is the skin layer of the molded article, is made as thin as possible, compared to the total thickness, by using a specific boron nitride.

Japanese Patent Publication Unexamined No. 94185/1971 discloses that boron nitride is added to polyoxymethylene. However, it does not disclose the specific boron nitride used in the present invention and the thin-walled injection molded article of the present invention.

An object of the present invention is to provide a thin-walled molded article of a polyacetal resin, whose dimensions change very little at a high temperature and humidity.

DISCLOSURE OF THE INVENTION

The present invention relates to a method for producing a thin-walled molded article of a polyacetal resin comprising adding 10 to 1000 ppm of boron nitride, having an average particle diameter of 1 to 10 μm and a content of diboron trioxide of 0.005 to 1.0% by weight, to a polyacetal resin and molding an article having a maximum wall thickness of 0.2 to 1 mm by injection molding.

In the present invention, the thin-walled molded article is a molded article having a maximum wall thickness of 0.2 to 1 mm. The molding method of the present invention is particularly useful for producing a thin-walled molded article having a maximum wall thickness of 0.25 to 0.6 mm.

The polyacetal resins to be used in the present invention include a polyacetal resin homopolymer consisting substantially of oxymethylene units, produced by using a formaldehyde monomer or a cyclic oligomer such as a trimer (trioxane), tetramer (tetraoxane) and the like as a raw material, and a polyacetal resin copolymer comprising 0.1 to 2% by weight of a oxyalkylene unit having 2 to 8 carbon atoms, produced by using the above raw material and cyclic ethers such as ethylene oxide, propylene oxide, epichlorohydrine, 1,3-dioxolane, a formal of a glycol, a formal of a diglycol and the like. The polyacetal resin further includes a branched polyacetal copolymer having a branched molecular chain and a block copolymer comprising 50% by weight or more of an oxymethylene repeating unit and other component blocks. In the present invention, if necessary, the above polyacetal resins can be used in combination. However, the polyacetal resin homopolymer or the polyacetal resin copolymer is preferably used alone in view of dimensional stability. The polyacetal resin homopolymer is more preferable.

The MFR measured under ASTM D1238-57 E condition of a polyacetal resin is preferably 40 g/10 min. or more, more preferably 60 g/10 min. or more, most preferably 70 to 100 g/10 min.

The present invention is characterized in injection molding a polyacetal comprising a specific boron nitride.

An average particle diameter of boron nitride to be used in the present invention is 1 to 10 μm, preferably 2 to 7 μm. A content of diboron trioxide is 0.005 to 1.0% by weight, preferably 0.05 to 0.7% by weight, more preferably 0.1 to 0.6% by weight. A mixing amount of diboron trioxide is 10 to 1000 ppm, preferably 10 to 300 ppm, more preferably 100 to 200 ppm, based on the amount of the polyacetal resin.

In the present invention, in order to impart necessary properties to the above polyacetal resin to be used for molding according to its application and object, known additives such as a polyamide, a stabilizer described in Japanese Patent publication Unexamined No. 247247/1990, a hindered phenol antioxidant, an ultraviolet absorber, a hindered amine weathering agent, an antistatic agent, a parting agent, a lubricant, an inorganic filler and the like can be added in the range which the purpose of the present invention is not impaired.

Time of crystallization of a mixture comprising the polyacetal resin, boron nitride and, if necessary, the additive, to be used for molding is preferably 100 seconds or less. Time of crystallization in the present invention is defined as follows. 5 mg of a sample of the polyacetal resin mixture is heated to 200° C. at a rate of 320° C./min. with a DSC, it is kept at 200° C. for 2 minutes and then, the sample is cooled to 150° C. at a rate of 80° C./min. Time of crystallization is the period (seconds) between the time when a temperature of a sample holder becomes 150° C. and the time when the top of a heat generation peak appears because of crystallization of the polyacetal resin.

When a polyacetal resin mixture having time of crystallization of more than 100 seconds is used, a molded article having excellent dimensional stability is not easily obtained. Time of crystallization is more preferably 10 to 70 seconds, most preferably 20 to 50 seconds.

The above polyacetal resin mixture is molded by injection molding into a molded article having a maximum wall thickness of 0.2 to 1 mm, preferably 0.25 to 0.6 mm. With respect to an injection molding method, conventional methods can be used. However, preferable injection molding methods are (1) a method having a mold temperature of 100° to 150° C., preferably 110° to 140° C. and (2) a method having a filling time of 1 second or less, preferably 0.5 second or less, more preferably 0.1 second or less.

The most preferable injection molding method is a method having a mold temperature of 100° to 150° C. and a filling time of 0.1 second or less.

It is observed with an electron microscope that the thin-walled molded article obtained by this invention has a maximum spherulite size of the polyacetal resin of 40 μm or less and a thickness of an amorphous layer, which is a skin layer of the molded article, of 200 μm or less.

The maximum spherulite size is defined as follows. A slice having a thickness of 10 μm is cut out of the molded article with a microtome. An about 340 magnification photograph of the crystalline part of the polyacetal resin molded article is taken with a transmission type polarized microscope using a crossed nicol. In case of diameters of spherulites being clearly identified (FIG. 3), the maximum spherulite size is the diameter of the largest spherulite among spherulites in the photograph. In case of diameters of spherulites not being clearly identified (FIG. 2), the maximum spherulite size is a value of twice the length of the maximal polarized monochrome parts of the spherulite among spherulites of which a polarized monochrome part (a part having the same color) does not connect with a polarized monochrone part of other spherulites and which are confirmed as particulate (the maximum length of a polarized monochrome part is regarded as the half of the spherulite diameter).

The amorphous layer is a layer, in which the spherulite is not found in the above polarized photomicrograph.

Among thin-walled molded articles obtained by the present invention, a maximum spherulite size of a molded article having good dimensional stability is 6 to 30 μm, more preferably 10 to 20 μm.

An amorphous layer thickness of the molded article having good dimensional stability is 50 μm or less, more preferably 5 μm or less.

According to the present invention, the molded article of the polyacetal resin having little warpage at a high temperature and humidity can be obtained.

The present invention is suitable for molding of a thin-walled gear, a thin walled cam, a thin-walled cam gear, a shutter and the like, which are used for the application requiring thin wall thickness and accuracy. Among the above molding, the present invention is suitable for molding of a shutter of a cartridge for a disk or tape.

The shutter of the cartridge for the disk or tape is a shutter attached to the outer face of a case having a built-in magnetic disk or tape in order to open and close a window for introducing a head.

Particularly, the present invention is most suitable for molding of a shutter of a floppy disk having a maximum wall thickness of 0.35 mm or less.

DESCRIPTION OF SYMBOLS

A: line caused by pasting photographs together
1: grain surface
2: mirror surface
a: angle
b: angle

BEST MODE FOR CARRYING OUT THE INVENTION

Examples 1 to 19 and Comparative Examples
1 to 21

Figure 1:
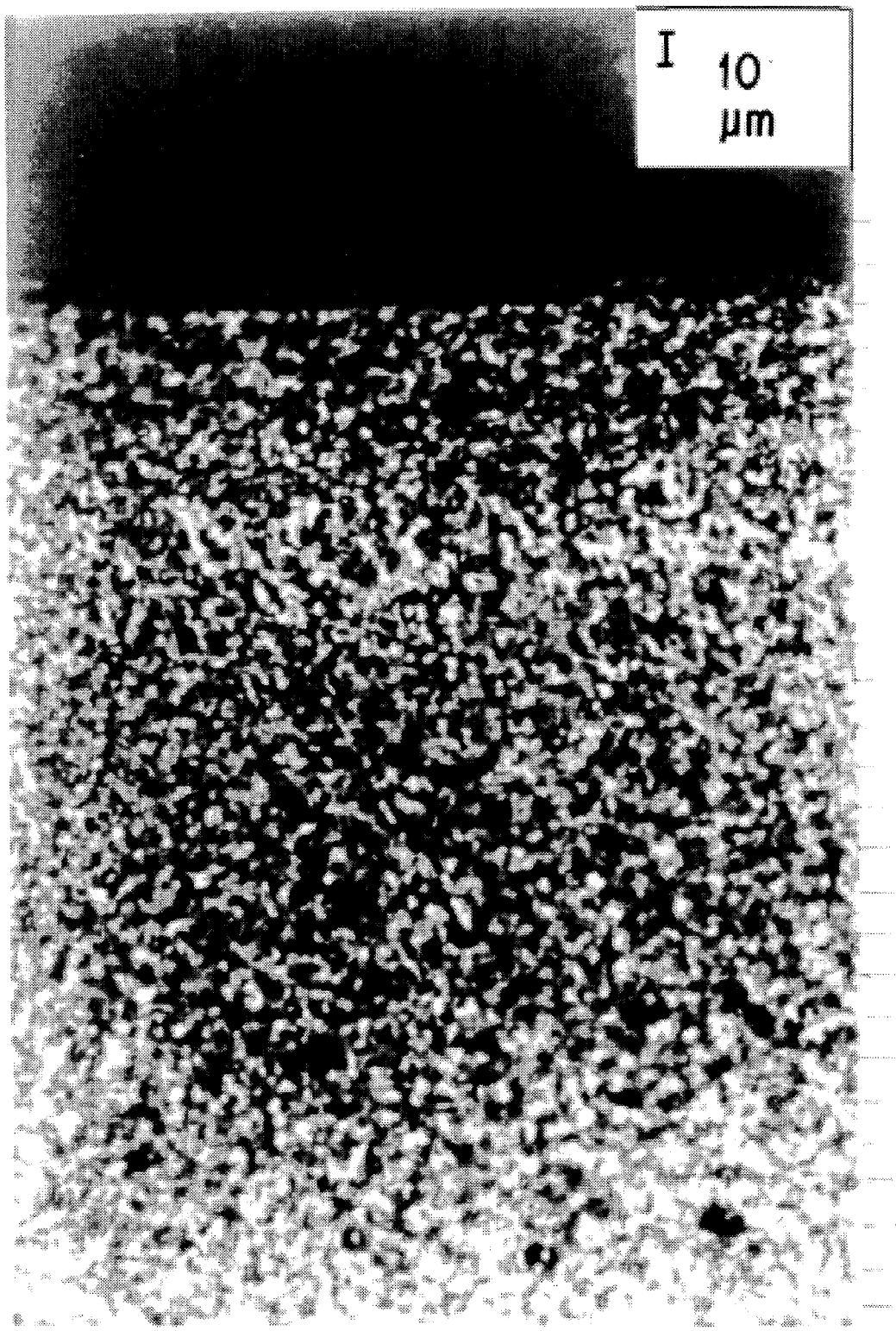
FIG. 1 is a photomicrograph showing one example of resin crystalline structure of a molded article of the present invention.
Figure 2:
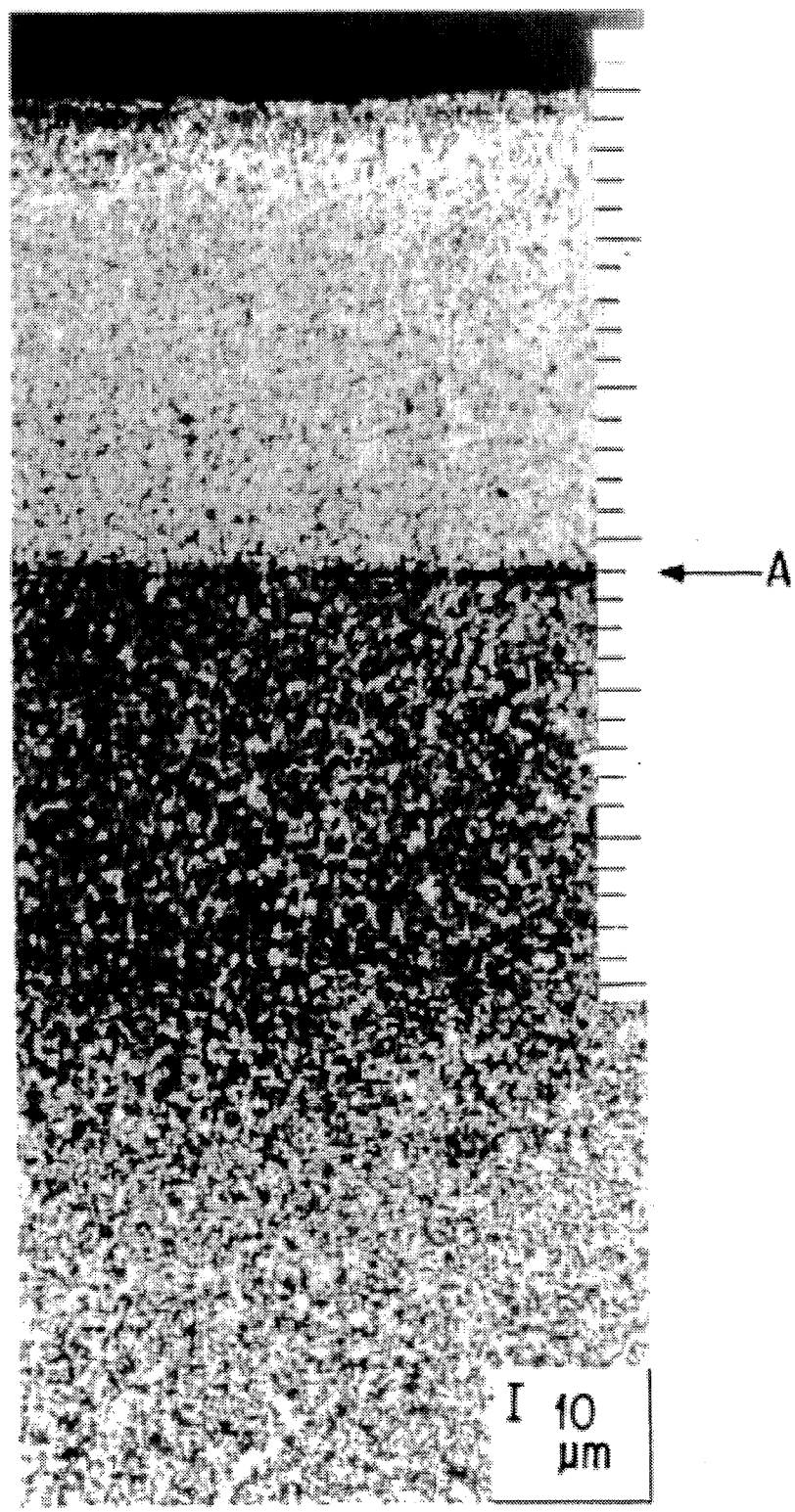
FIG. 2 is a photomicrograph showing another example of resin crystalline structure of a molded article of the present invention.
Figure 3:
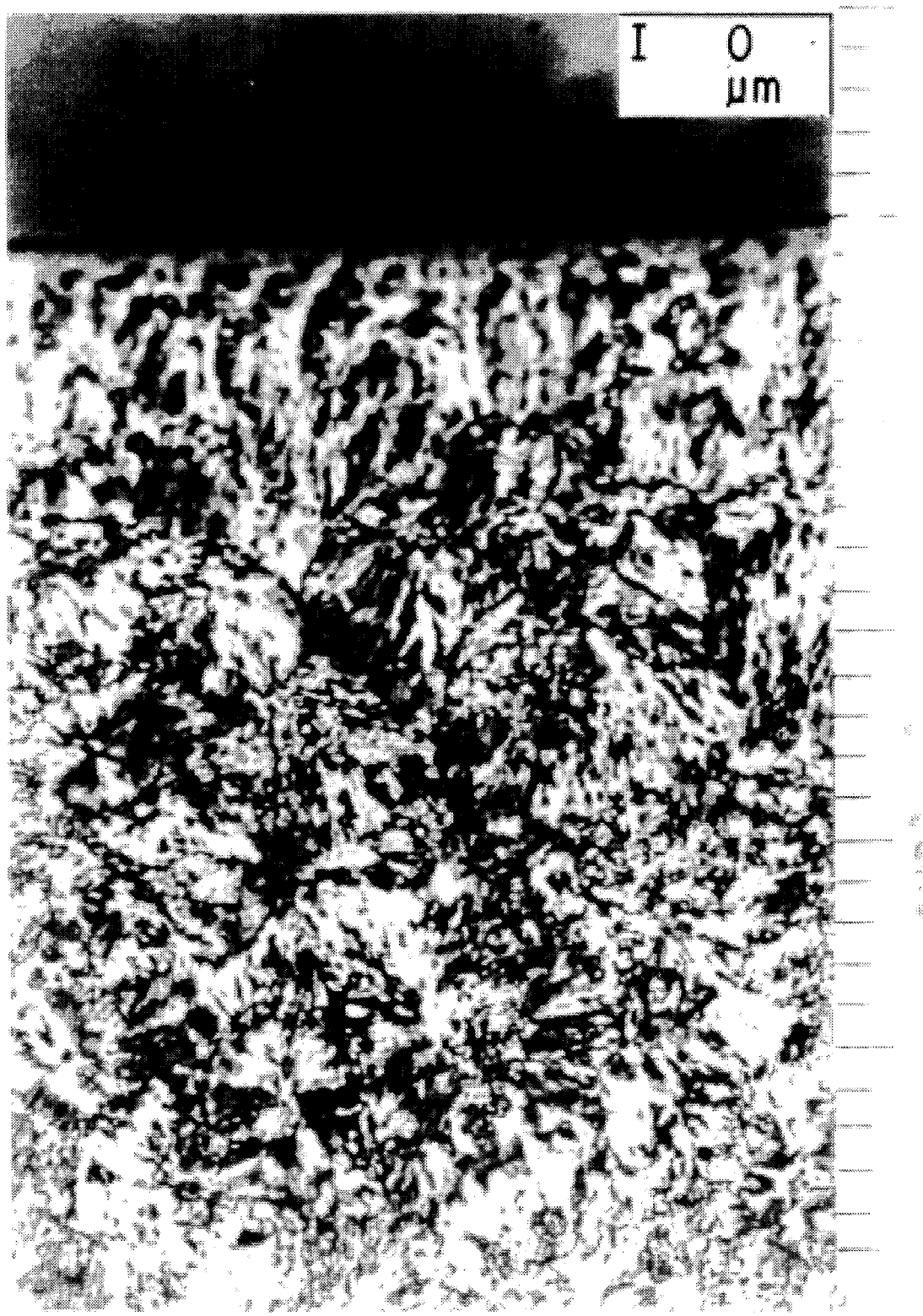
FIG. 3 is a photomicrograph showing resin crystalline structure of a molded article obtained in Comparative Example.
Figure 4:
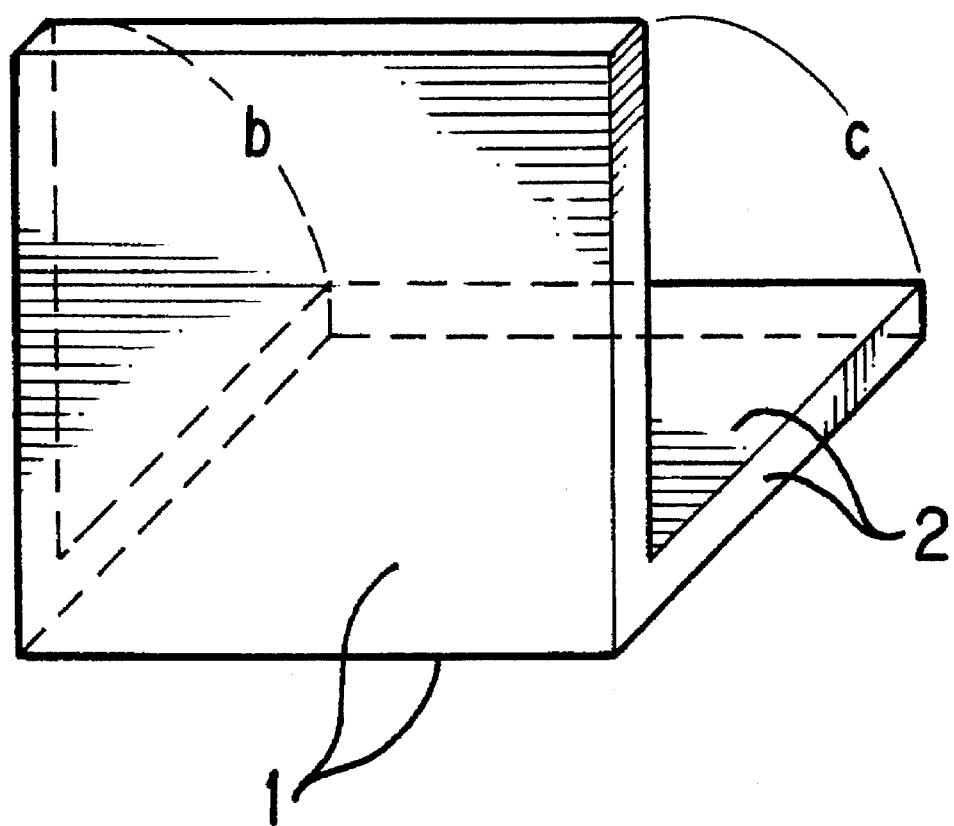
FIG. 4 is a perspective view of form of a molded article, whose demensional change and the like are measured in the present invention.

Powders of polyacetal homopolymers acetylated at both ends were produced according to a method described in U.S. Pat. No. 2,998,409. MFRs of the polyacetal homopolymers were 30 to 110 g/10 min. under ASTM D1238-57 E condition. The powders of the polyacetal homopolymers were dried at 80° C. for 3 hours. 0.2% by weight of IRGANOX 245 manufactured by Ciba-Geigy Ltd. as a antioxidant and at least one selected from boron nitride, talc, calcium carbonate and nylon 6,6 were incorporated into the resultant powder as shown in Tables 1 to 5. The resultant mixture was melt kneaded with a twin-screw vented extruder having a temperature of 190° C., a screw revolution speed of 50 rpm, a discharge amount of 3 kg/hour. After pellets cut with a cutter were dried at 80° C. for 3 hours again, a molded article shown in FIG. 4 was produced with a 3 ounce injection molding machine having a mold temperature of 110° C. and a filling time of 0.2 second. The molded article has a shape formed by binding two boards having a size of 5 cm×5 cm at each one side, and having an angle of 90° between two boards and two outer surfaces subjected to processing of GR003, which is a grain pattern of Tanazawa Hakko-sha. The wall thickness of the molded article can be changed in the range of 0.1 to 5 mm.

After molding, the molded article was left at 23° C. and a humidity of 50% for 2 days, further left under an atmosphere of a high temperature of 60° C. and a high humidity of 80% for 6 hours and finally left under an atmosphere of 23° C. and a humidity of 50% for 1 hour. Before putting the molded article under an atmosphere of 60° C. and a humidity of 80%, angles a and b of the molded article were shown in FIG. 4. The angles a and b, which became the largest angles within 1 hour after taking the molded article out of an atmosphere of 60° C. and a humidity of 80%, and putting it under an atmosphere of 23° C. and a humidity of 50%, were angles a' and b' respectively. The larger of (a'—a) and (b'—b) was measured as a maximum warpage angle. Before putting the molded article under an atmosphere of 60° C. and a humidity of 80%, the maximum spherulite size, the maximum thickness of the amorphous layer, which were determined among those measured on 5 spots of the molded article, and time of crystallization were measured according to the above methods.

These results are shown in Tables 1 to 5.

Example 20

A copolymer of an acetal comprising 2.8% of ethylene oxide was prepared according to a method described in U.S. Pat. No. 3,027,352. The MFR of the polymer was 40 g/10 min. under ASTM D1238-57 E condition. The acetal copolymer was dried at 80° C. for 3 hours. 0.2% by weight of IRGANOX245 manufactured by Ciba-Geigy Ltd. as antioxidant and 100 ppm of boron nitride having a content of 0.1% by weight of diboron trioxide were incorporated into the dried acetal copolymer. A molded article having a maximum wall thickness of 1 mm was obtained according to the same method as in Example 1.

Warpage of the molded article obtained in this way was measured according to the same method as in Example 1. The warpage was 0.4°.

The maximum spherulite size of the polyacetal resin composing the molded article was 25 μm. The thickness of the amorphous layer was 6 μm. Time of crystallization was 70 seconds.

Example 21

A shutter having a maximum wall thickness of 0.35 mm was molded with a mold for a shutter of a 3.5 inch floppy disk by using the same polymer mixture as used in Example 3.

The shutter obtained with a 3 ounce molding machine having a mold temperature of 100° C. and a filling time of 0.1 second was left under an atmosphere of a high temperature of 60° C. and a high humidity of 80% for 6 hours and finally left under an atmosphere of 23° C. and a humidity of 50% for 1 hour. Warpage of 4 corners of the shutter was measured according to the above method. An angle of the largest warpage was less than 0.1°.

TABLE 1

| Example | Type of additives except for antioxidant (amount) | Polyacetal resin Type | MFR (g/10 min.) | Molded article Maximum wall thickness (mm) | Time of crystallization (sec.) | Maximum spherulite size (μm) | Amorphous layer (μm) | Warpage (degree) | Fig. |
|---|---|---|---|---|---|---|---|---|---|
| 1 | Boron nitride (10 ppm) ($B_2O_3$: 0.1%, average particle diameter: 2 μm) | Homo-polymer | 40 | 1 | 100 | 40 | 200 | 0.8 | — |
| 2 | Boron nitride (50 ppm) ($B_2O_3$: 0.1%, average particle diameter: 2 μm) | Homo-polymer | 40 | 1 | 70 | 30 | 50 | 0.4 | — |
| 3 | Boron nitride (100 ppm) ($B_2O_3$: 0.1%, average particle diameter: 2 μm) | Homo-polymer | 40 | 1 | 50 | 18 | 3 | 0.2 | 1 |
| 4 | Boron nitride (200 ppm) ($B_2O_3$: 0.1%, average particle diameter: 2 μm) | Homo-polymer | 40 | 1 | 20 | 10 | 3 | 0.3 | — |
| 5 | Boron nitride (300 ppm) ($B_2O_3$: 0.1%, average particle diameter: 2 μm) | Homo-polymer | 40 | 1 | 12 | 6 | 3 | 0.6 | — |
| 6 | Boron nitride (1000 ppm) ($B_2O_3$: 0.1%, average particle diameter: 2 μm) | Homo-polymer | 40 | 1 | 12 | 6 | 3 | 0.8 | — |
| 7 | Boron nitride (10 ppm) ($B_2O_3$: 0.1%, average particle diameter: 2 μm) | Homo-polymer | 10 | 1 | 80 | 28 | 150 | 0.9 | — |
| 8 | Boron nitride (10 ppm) ($B_2O_3$: 0.1%, average particle diameter: 2 μm) | Homo-polymer | 30 | 1 | 73 | 25 | 120 | 0.8 | — |
| 9 | Boron nitride (10 ppm) ($B_2O_3$: 0.1%, average particle diameter: 2 μm) | Homo-polymer | 40 | 1 | 70 | 16 | 30 | 0.3 | — |
| 10 | Boron nitride (10 ppm) ($B_2O_3$: 0.1%, average particle diameter: 2 μm) | Homo-polymer | 70 | 1 | 68 | 16 | 5 | 0.1 | — |
| 11 | Boron nitride (10 ppm) ($B_2O_3$: 0.1%, average particle diameter: 2 μm) | Homo-polymer | 100 | 1 | 67 | 10 | 2 | 0.1 | 2 |
| 12 | Boron nitride (10 ppm) ($B_2O_3$: 0.1%, average particle diameter: 2 μm) | Homo-polymer | 110 | 1 | 65 | 6 | 6 | 0.7 | — |
| 13 | Boron nitride (100 ppm) ($B_2O_3$: 0.005%, average particle diameter: 2 μm) | Homo-polymer | 40 | 1 | 80 | 25 | 10 | 0.9 | — |
| 14 | Boron nitride (100 ppm) ($B_2O_3$: 1.0%, average particle diameter: 2 μm) | Homo-polymer | 40 | 1 | 70 | 25 | 7 | 0.9 | — |

TABLE 2

| Example | Type of additives except for antioxidant (amount) | Polyacetal resin Type | MFR (g/10 min.) | Molded article Maximum wall thickness (mm) | Time of crystallization (sec.) | Maximum spherulite size (μm) | Amorphous layer (μm) | Warpage (degree) |
|---|---|---|---|---|---|---|---|---|
| 15 | Boron nitride (100 ppm) ($B_2O_3$: 0.1%, average particle diameter: 2 μm) | Homo-polymer | 40 | 0.8 | 50 | 18 | 3 | 0.2 |
| 16 | Boron nitride (100 ppm) ($B_2O_3$: 0.1%, average | Homo-polymer | 40 | 0.6 | 50 | 18 | 3 | 0.1 |

TABLE 2-continued

| Example | Type of additives except for antioxidant (amount) | Polyacetal resin Type | MFR (g/10 min.) | Molded article Maximum wall thickness (mm) | Time of crystallization (sec.) | Maximum spherulite size (μm) | Amorphous layer (μm) | Warpage (degree) |
|---|---|---|---|---|---|---|---|---|
| 17 | Boron nitride (100 ppm) (B₂O3: 0.1%, average particle diameter: 2 μm) | Homo-polymer | 40 | 0.35 | 50 | 18 | 3 | 0.06 |
| 18 | Boron nitride (100 ppm) (B₂O3: 0.1%, average particle diameter: 2 μm) | Homo-polymer | 40 | 0.25 | 50 | 18 | 3 | 0.1 |
| 19 | Boron nitride (100 ppm) (B₂O3: 0.1%, average particle diameter: 2 μm) | Homo-polymer | 40 | 0.2 | 50 | 18 | 3 | 0.2 |

TABLE 3

| Comparative Example | Type of additives for antioxidant (amount) | Polyacetal resin Type | MFR (g/10 min.) | Molded article Maximum wall thickness (mm) | Time of crystallization (sec.) | Maximum spherulite size (μm) | Amorphous layer (μm) | Warpage (degree) | Fig. |
|---|---|---|---|---|---|---|---|---|---|
| 1 | — | Homo-polymer | 40 | 1 | 230 | 100 | 300 | 22 | — |
| 2 | Boron nitride (2 ppm) (B₂O3: 0.1%, average particle diameter: 2 μm) | Homo-polymer | 40 | 1 | 200 | 90 | 210 | 18 | — |
| 3 | Boron nitride (5 ppm) (B₂O3: 0.1%, average particle diameter: 2 μm) | Homo-polymer | 40 | 1 | 150 | 70 | 205 | 17 | — |
| 4 | Boron nitride (5 ppm) (B₂O3: 0.1%, average particle diameter: 2 μm) | Homo-polymer | 40 | 0.25 | 150 | 50 | 100 | 30 | — |
| 5 | Boron nitride (5 ppm) (B₂O3: 0.1%, average particle diameter: 2 μm) | Homo-polymer | 40 | 0.6 | 150 | 70 | 205 | 28 | — |
| 6 | Boron nitride (5 ppm) (B₂O3: 0.1%, average particle diameter: 2 μm) | Homo-polymer | 40 | 2 | 150 | 70 | 205 | 10 | — |
| 7 | Boron nitride (5 ppm) (B₂O3: 0.1%, average particle diameter: 2 μm) | Homo-polymer | 40 | 3 | 150 | 70 | 205 | 3 | — |
| 8 | Boron nitride (1100 ppm) (B₂O3: 0.1%, average particle diameter: 2 μm) | Homo-polymer | 40 | 1 | 8 | 6 | 3 | 2 | — |
| 9 | calcium carbonate (1000 ppm) (avrage particle diameter: 1 μm) | Homo-polymer | 40 | 1 | 100 | 70 | 10 | 5 | 3 |
| 10 | talc (1500 ppm) (average) particle | Homo-polymer | 40 | 1 | 98 | 45 | 210 | 2 | — |
| 11 | diameter: 5 μm) nylon 6,6 (5000 ppm) (average particle diameter: 4 μm) | Homo-polymer | 40 | 1 | 95 | 45 | 210 | 3 | — |

TABLE 4

| Comparative Example | Type of additives except for antioxidant (amount) | Polyacetal resin Type | MFR (g/10 min.) | Molded article Maximum wall thickness (mm) | Time of crystallization (sec.) | Maximum spherulite size (μm) | Amorphous layer (μm) | Warpage (degree) |
|---|---|---|---|---|---|---|---|---|
| 12 | Boron nitride (10 ppm) (B₂O₃: 0.1%, average particle diameter: 2 μm) | Homo-polymer | 30 | 2 | 73 | 25 | 120 | 3 |
| 13 | Boron nitride (10 ppm) (B₂O₃: 0.1%, average particle diameter: 2 μm) | Homo-polymer | 30 | 3 | 73 | 25 | 120 | 4 |
| 14 | Boron nitride (10 ppm) | Homo- | 30 | 0.15 | 73 | 10 | 70 | 2 |

TABLE 4-continued

| Comparative Example | Type of additives except for antioxidant (amount) | Polyacetal resin Type | MFR (g/10 min.) | Molded article Maximum wall thickness (mm) | Time of crystallization (sec.) | Maximum spherulite size (μm) | Amorphous layer (μm) | Warpage (degree) |
|---|---|---|---|---|---|---|---|---|
| | (B₂O₃: 0.1%, average particle diameter: 2 μm) | polymer | | | | | | |
| 15 | Boron nitride (100 ppm): (B₂O₃: 0.1%, avrage particle diameter: 2 μm) | Homo-polymer | 40 | 2 | 50 | 18 | 3 | 3 |
| 16 | Boron nitride (100 ppm) (B₂O₃: 0.1%, avrage particle diameter: 2 μm) | Homo-polymer | 40 | 3 | 50 | 18 | 3 | 4 |
| 17 | Boron nitride (100 ppm) (B₂O₃: 0.1%, avrage particle diameter: 2 μm) | Homo-polymer | 40 | 0.15 | 50 | 18 | 3 | 2 |

TABLE 5

| Comparative Example | Type of additives except for antioxidant (amount) | Polyacetal resin Type | MFR (g/10 min.) | Molded article Maximum wall thickness (mm) | Time of crystallization (sec.) | Maximum spherulite size (μm) | Amorphous layer (μm) | Warpage (degree) |
|---|---|---|---|---|---|---|---|---|
| 18 | Boron nitride (100 ppm) (B₂O₃: 0.002%, average particle diameter: 2 μm) | Homo-polymer | 40 | 1 | 110 | 20 | 210 | 3 |
| 19 | Boron nitride (100 ppm) (B₂O₃: 1.2%, average particle diameter: 2 μm) | Homo-polymer | 40 | 1 | 120 | 30 | 210 | 4 |
| 20 | Boron nitride (100 ppm) (B₂O₃: 0.1%, average particle diameter: 11 μm) | Homo-polymer | 40 | 1 | 200 | 60 | 200 | 9 |
| 21 | Boron nitride (100 ppm) (B₂O₃: 0.1%, avrage particle diameter: 0.6 μm) | Homo-polymer | 40 | 1 | 200 | 50 | 210 | 5 |

We claim:

1. A method for producing a thin-walled molded article of a polyacetal resin comprising adding 10 to 1000 ppm of boron nitride having an average particle diameter of 1 to 10 μm and a content of diboron trioxide of 0.005 to 1.0% by weight to a polyacetal resin and molding an article having a maximum wall thickness of 0.2 to 1 mm by injection molding.

2. The method of claim 1 wherein the thin-walled molded article of the polyacetal resin is a shutter of a cartridge for a disk or tape.

* * * * *